US010583081B1

(12) United States Patent
Myers

(10) Patent No.: US 10,583,081 B1
(45) Date of Patent: Mar. 10, 2020

(54) APPARATUS AND FORMULATION FOR TREATING MOUTH ULCERS

(71) Applicant: Richard A. Myers, Lumberton, MS (US)

(72) Inventor: Richard A. Myers, Lumberton, MS (US)

( * ) Notice: Subject to any disclaimer, the term of this patent is extended or adjusted under 35 U.S.C. 154(b) by 0 days.

(21) Appl. No.: 16/201,986

(22) Filed: Nov. 27, 2018

Related U.S. Application Data

(60) Provisional application No. 62/590,949, filed on Nov. 27, 2017.

(51) Int. Cl.

| | |
|---|---|
| ***A61K 31/56*** | (2006.01) |
| ***A61K 9/00*** | (2006.01) |
| ***A61K 31/4453*** | (2006.01) |
| ***A61C 19/06*** | (2006.01) |
| ***A61K 31/215*** | (2006.01) |
| ***A61K 9/16*** | (2006.01) |
| ***A61K 31/573*** | (2006.01) |

(52) U.S. Cl.
CPC ............ *A61K 9/006* (2013.01); *A61C 19/063* (2013.01); *A61K 9/16* (2013.01); *A61K 31/215* (2013.01); *A61K 31/4453* (2013.01); *A61K 31/573* (2013.01)

(58) Field of Classification Search
None
See application file for complete search history.

(56) References Cited

U.S. PATENT DOCUMENTS

| | | | | |
|---|---|---|---|---|
| 6,319,513 | B1 * | 11/2001 | Dobrozsi ............. | A61K 9/0043 424/434 |
| 2005/0239019 | A1 * | 10/2005 | Hall ....................... | A61C 17/02 433/229 |
| 2007/0020299 | A1 * | 1/2007 | Pipkin .................. | A61K 9/0078 424/400 |

* cited by examiner

*Primary Examiner* — Shobha Kantamneni
(74) *Attorney, Agent, or Firm* — Brett Bartel

(57) ABSTRACT

A kit that is made of an apparatus comprising a bottle and a nozzle sprayer, and a pharmaceutical formulation comprising dyclonine HCL, triamcinolone, dicyclomine, and dental powder.

A method for treating mouth ulcers comprising administering to a patient a formulation comprising dyclonine HCL, triamcinolone, dicyclomine, and dental powder to an affected area.

7 Claims, 1 Drawing Sheet

APPARATUS AND FORMULATION FOR TREATING MOUTH ULCERS

CROSS-REFERENCE TO RELATED APPLICATIONS

This present application claims the priority of U.S. Provisional Patent Application Ser. No. 62/590,949 filed Nov. 27, 2017; the entire content and scope of which are incorporated herein by reference.

FIELD

The present disclosure generally relates to a kit and a pharmaceutical formulation for treating recurrent mouth ulcers.

BACKGROUND

Mouth ulcers are problematic to treat due to the painful and awkward nature of applying known treatments. A kit and a pharmaceutical formulation may be used that facilitates treatment in a convenient, pain free manner.

SUMMARY

A kit that is made of an apparatus that is made of a bottle, an adjustable nozzle, and a sprayer, and is filled with a pharmaceutical formulation comprising dyclonine HCL, triamcinolone, dicyclomine, and dental powder.

A method for treating mouth ulcers comprising administering to a patient a formulation comprising dyclonine HCL, triamcinolone, dicyclomine, and dental powder to an affected area in one spray four times a day for thirty days, or until the symptoms have resolved.

A method for treating mouth ulcers comprising administering to a patient a formulation comprising an oral anesthetic, a corticosteroid, an anticholinergic, and dental powder to an affected area in one spray four times a day for thirty days, or until the symptoms have resolved.

DESCRIPTION OF THE FIGURES

The features and components of the following figures are illustrated to emphasize the general principles of the present disclosure and are not necessarily drawn to scale. Corresponding features and components throughout the figures may be designated by matching reference characters for the sake of consistency and clarity.

DETAILED DESCRIPTION

Figure 1:
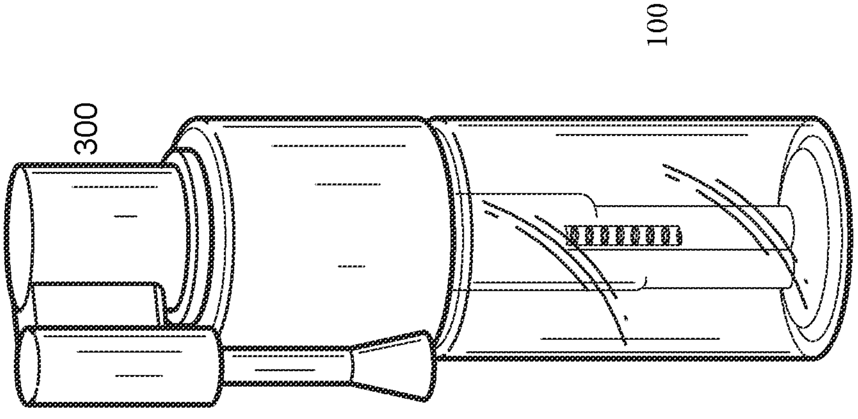
FIG. 1 is an apparatus with an adjustable nozzle in the stored position.

The present disclosure will now be described more fully hereinafter with reference to the accompanying drawings, in which some, but not all embodiments of the disclosure are shown. Indeed, this disclosure may be embodied in many different forms and should not be construed as limited to the embodiments set forth hereinafter; rather, these embodiments are provided so that this disclosure will satisfy applicable legal requirements. Like numbers refer to like elements throughout.

The present disclosure recognizes that dentists are very limited on the medications they can prescribe for aphthous stomatitis or mouth ulcers and that most over-the-counter ("OTC") products only treat the symptoms not the cause. About half of the population get mouth ulcers. There are various forms of mouth ulcers, and some usually heal within a couple of weeks and do not leave scars. For most people, they are just annoying. But some people get larger sores (almost one-half inch across or larger). These take longer to heal, can be painful, and may leave scars. These ulcers may be so uncomfortable that it is sometimes hard to eat or speak.

There are many different types of mouth sores than can develop around or in the mouth. Some are painful, some are unsightly and some may be a sign of something more serious.

Mouth ulcers are usually round or oval sores that commonly appear inside the mouth on the cheeks, lips, tongue. They can be white, red, yellow or grey in color and swollen. It's possible to have more than one mouth ulcer at a time and they may spread or grow.

Mouth ulcers shouldn't be confused with cold sores, which are small blisters that develop on the lips or around the mouth. Cold sores often begin with a tingling, itching or burning sensation around your mouth. Canker sores are small, white or yellow, center lesions with a red border. They develop in the mouth on the tongue, inside cheek areas, lips, gum line and throat area. They are not contagious. Cold sores may appear as clusters of red, raised blisters outside the mouth—typically around the lips, but they can develop under the nose or under the chin. Cold sores may be highly contagious.

Typically, only the symptoms of mouth ulcers can be treated. Treatment is meant to alleviate the symptoms and the pain of an ulcer. Treatment does not stop a person from having mouth sores again.

Large or very painful sores may be treated with steroid medicines. Steroid medications may be gels or creams. These gels or creams are placed on the sores. Many steroid medicines do help make the ulcers or the sores heal faster. Steroid medicines also inhibit the growth of the sores. In addition to creams and gels, steroids medicines may also be injected. There are also a few medicines you can take by mouth, but this is for the most serious cases. However, these creams, ointments, and rinses are often either painful or awkward to apply.

The present disclosure illustrates a treatment of mouth ulcers in a manner that does not cause pain or discomfort to a patient. The treatment requires an apparatus, which delivers a pharmaceutical formulation 200.

The apparatus is shown in the Figures. The apparatus contains a bottle 100 where the formulation 200 is stored. The apparatus also contains an adjustable nozzle 300 and a sprayer 400 by which the apparatus may spray the pharmaceutical formulation 200 to the affected areas. The pharmaceutical formulation 200 may be applied without touching the inflamed, painful areas.

Presently, there is no multi-ingredient ulcer medication in the US. The pharmaceutical formulation 200 of the present disclosure uses the combination of four ingredients: dyclonine HCL, triamcinolone, dicyclomine, and dental powder.

Dyclonine HCL is an oral anesthetic that is the active ingredient of Sucrets, which is an OTC throat lozenge for sore throats. Dyclonine HCL is also found in some varieties of the Cepacol sore throat spray. Dyclonine HCL is a local anesthetic and in the present pharmaceutical formulation 200 is in the form of a hydrochloride salt for topical application.

Dyclonine HCL has also been used as a self-medication for the short-term relief of minor sore throat pain and mouth and gum irritation. Dyclonine HCL has also been used in fixed combination with menthol as self-medication for temporary relief of occasional minor irritation, pain, or soreness of mouth or throat, as well as for treatment for coughs associated with a cold or inhaled irritants.

Dyclonine HCL has also been used as a local anesthetic agent prior to laryngoscopy, bronchoscopy, esophagoscopy, or endotracheal intubation. However, oral solutions no longer are commercially available in the US.

Dyclonine HCL may be administered orally as a lozenge. When used as a lozenge, it should be allowed to slowly dissolve in the mouth. The patient should not bite or chew it.

Adults may take 1 lozenge in the amount of 1.2 mg, 2 mg, or 3 mg. A patient may repeat after 2 hours if necessary.

Traditionally, Dyclonine HCL was provided in a tablet or capsule. In the present formulation, the dyclonine is preferably in dry powder form to facilitate mixture with the other pharmaceutical compounds as well as to facilitate the apparatus in spraying the pharmaceutical formulation 200 on the affected areas.

Dyclonine HCL may be provided in the pharmaceutical formulation 200 in any amount ranging between 0.2 mg to 2 g. In one aspect, the amount of Dyclonine HCL in the formulation is 100 mg. In one aspect, the amount of Dyclonine HCL in the pharmaceutical formulation 200 is an amount between 75 mg and 125 mg.

Triamcinolone is a synthetic corticosteroid and derivative of cortisol (hydrocortisone) and is also known as 1-dehydro-9α-fluoro-16α-hydroxyhydrocortisone or 9α-fluoro-16α-hydroxyprednisolone as well as 9α-fluoro-11β,16α,17α,21-tetrahydroxypregna-1,4-diene-3,20-dione.

Triamcinolone acetonide is a synthetic corticosteroid used topically to treat various skin conditions, to relieve the discomfort of mouth sores and intraarticularly by proceduralists to treat various joint conditions.

Triamcinolone is used to treat a variety of skin conditions (e.g., eczema, dermatitis, allergies, rash). Triamcinolone reduces the swelling, itching, and redness that can occur in these types of conditions. Triamcinolone is a medium-to strong-potency corticosteroid.

Triamcinolone is an intermediate-acting synthetic glucocorticoid given orally, by injection, by inhalation, or as a topical ointment or cream.

Triamcinolone is used to treat a number of different medical conditions, such as eczema, Lichen sclerosus, psoriasis, arthritis, allergies, ulcerative colitis, lupus, sympathetic ophthalmia, temporal arteritis, uveitis, ocular inflammation, Urushiol-induced contact dermatitis, aphthous ulcers (usually as triamcinolone acetonide), visualization during vitrectomy and the prevention of asthma attacks. It will not treat an asthma attack once it has already begun. Triamcinolone has also been used off-label for macular degeneration.

Different triamcinolone derivatives are available, including acetonide, benetonide, furetonide, hexacetonide and diacetate. Triamcinolone acetonide is a more potent type of triamcinolone, being about eight times as effective as prednisone.

Triamcinolone should only be used on the skin. Under traditional uses, it is not used on the face, groin, or underarms unless directed by a doctor.

Under traditional applications and treatments, before applying triamcinolone, the administrator should wash and dry his or her hands. Before the medication is applied, the patient should clean and dry the affected area. The administrator should apply a thin film of the medication to the affected area and gently rub in, usually 2 to 4 times daily or as directed by a physician. It is also unwise to cover, bandage or wrap the area unless directed to do so by a physician. Triamcinolone should not be applied to the diaper area on an infant, nor used in tight-fitting diapers or plastic pants. After applying the medication, the administrator must wash his or her hands—unless the medication to treat the hands. When applying this medication near the eyes, the administrator should avoid getting it in the eyes of the patient as this may worsen or cause glaucoma. The nose or mouth should also be avoided. If a patient gets triamcinolone in his or her eyes, nose, or mouth, he or she should rinse with plenty of water. triamcinolone should only be used for the condition prescribed. Triamcinolone should not be used longer than prescribed.

Since administration of triamcinolone can be problematic, the present disclosure is an improvement on the delivery of triamcinolone to an affected area. Triamcinolone, in a dry, powder form, may be mixed with dyclonine HCL, dicyclomine, and dental powder yielding a dry powder form. The sprayer 400 from the apparatus will apply the pharmaceutical formulation 200 in a manner that is not painful nor inconvenient or awkward.

The pharmaceutical formulation 200 may contain an amount of triamcinolone ranging in any amount from 0.1 g to 1 g. In one aspect, the pharmaceutical formulation 200 contains 50 mg. In one aspect, the pharmaceutical formulation 200 contains an amount between 40 mg and 60 mg. The triamcinolone should be in a dry, powder form to blend with the other ingredients of the pharmaceutical formulation 200 to allow the sprayer 400 spray the pharmaceutical formulation 200 in dry powder form.

Dicyclomine belongs to a class of drugs known as anticholinergics/antispasmodics. Anticholinergics are a broad group of medicines that act on the neurotransmitter, acetylcholine. They are also called antispasmodics.

By blocking the action of acetylcholine, anticholinergics prevent impulses from the parasympathetic nervous system from reaching smooth muscle and causing contractions, cramps or spasms. Anticholinergics are used in the treatment of some gastrointestinal and bladder conditions. Anticholinergics may also be used in the treatment of some respiratory or movement disorders.

Dicyclomine affects specific muscles in the stomach and intestines called the smooth muscles. Dicyclomine helps to relax these muscles to relieve the spasms that functional bowel disorders cause in parts of the digestive system. Dicyclomine is used to treat spasms in the stomach caused by functional bowel disorders such as irritable bowel syndrome.

Dicyclomine in an oral tablet may cause drowsiness. A patient taking dicyclomine shouldn't do anything that requires him or her to be mentally alert, such as driving or operating machinery, until he or she knows how this drug affects him or her. Dicyclomine drug may also cause other side effects.

Antacids lower the absorption of dicyclomine. Dicyclomine may affect the absorption of other products such as levodopa, certain azole anti-fungal drugs (ketoconazole, itraconazole), slowly-dissolving forms of digoxin, among others. If a patient is taking either ketoconazole or itraconazole, he or she should take it at least 2 hours before dicyclomine. Many other drugs that also cause dry mouth and constipation may interact with anticholinergics/antispasmodics such as dicyclomine.

Dicyclomine is usually provided as a capsule, tablet, or liquid.

The present pharmaceutical formulation 200 may include an anticholinergic or antispasmodic. In one aspect, the anticholinergenic is dicyclomine.

Since absorption of dicyclomine may be affected by other compounds, the application of the pharmaceutical formulation 200 through the sprayer 400 of the adjustable nozzle of the apparatus containing the pharmaceutical formulation 200 will avoid the pitfalls of malabsorption as the present forms do.

The pharmaceutical formulation 200 may contain an amount of dicyclomine ranging in any amount from 0.1 mg to 1 g. In one aspect, the pharmaceutical formulation 200 contains 50 mg of dicyclomine. In one aspect, the pharmaceutical formulation 200 contains an amount between 40 mg and 60 mg of dicyclomine. The dicyclomine within the pharmaceutical formulation 200 will be in a dry form so as to be able to be sprayed in a dry powder through the sprayer 400.

Dental powder is mixture of a variety of ingredients often to replace toothpaste as a cleaning substance or mixed with medicines to facilitate administration to an affected area. Dental powers may contain baking soda, herbs like cloves, mint, or cinnamon, and an artificial sweetener for taste.

The first use of dental powder was made from burnt eggshells mixed with pumice and the power of ox hooves' ashes. Later herbs, salt, and *ginseng* were added to enhance the cleaning properties and taste of the powder. Some ancient powders used crushed bones and oyster shells to make a grittier powder. To prevent bad breath, the Romans also added powdered bark and charcoal to their teeth cleaner. Later, they created a milder substance using burnt snail shells, herbs, and honey.

Many dental powders contain baking soda as the key component. Though some rudimentary powders still contained abrasive substances like brick dust, earthenware, and cuttlefish to thoroughly polish teeth. Later borax was added to provide a cleansing, foaming effect and glycerin turns the powder into a paste.

Various modern dental powders are known in the art.

The dental powder will be added to the dyclonine HCL, triamcinolone, and dicyclomine so that the pharmaceutical formulation 200 is in powdered form and fit to be sprayed through the sprayer 400 and suctioned through the adjustable nozzle 300 of the bottle 100.

Dental powder may be provided in the pharmaceutical formulation 200 in any amount ranging between 0.1 g to 10 g. In one aspect, the amount of dental powder in the pharmaceutical formulation 200 is 300 mg. In one aspect, the amount of dental powder in the pharmaceutical formulation 200 is an amount between 250 mg to 325 mg.

When the pharmaceutical formulation 200 is delivered by the apparatus, it applies a numbing agent (reduces pain), a low-potency steroid (helps to reduce swelling), an anti-viral (to improve the cause), and coats the affected area making it slick to improve the patients' short term and long-term effects of having ulcers.

The delivery process is also one that will allow for ease of application of the medication to all areas of the mouth.

The dry powder dispenser accurately blows/lays the powder on to the affected ulcer and begins to numb.

The apparatus and pharmaceutical formulation 200, or kit, allows for an "ouchless" application of the medication directly to the affected area. As with past ulcer OTC treatment such as cremes and mouth rinses were painful and awkward to apply to the affected ulcer area. Ulcers in the very back of the mouth, top of the gum line and under the tongue were nearly impossible to correctly apply cremes to. When applied correctly, the kit can reach the affected areas within the mouth and under the tongue with ease.

The kit may contain the pharmaceutical formulation 200 already mixed in the bottle 100, or it may require a pharmacist to mix the pharmaceutical formulation 200 from the active ingredients before dispensing the kit to a patient.

In order to mix the pharmaceutical formulation 200, a pharmacist should open bottle 100 of Triamcinolone Powder 0.5 g, Acyclovir Powder 1.1 g, and Dicyclomine Powder 0.1 g.

Then the pharmacist will open the puffer dispenser and add all of the powder contents of the triamcinolone to the puffer dispenser.

Then the pharmacist will tap all contents out of the vial; and then add all of the powder contents of the acyclovir to the puffer dispenser.

Then the pharmacist will tap all contents out of the vial; and shake the puffer dispenser gently mixing the powders together.

Then the pharmacist will add all of the powder contents of the dicyclomine to the puffer dispenser.

Then the pharmacist will tap all contents out of the vial; and shake the puffer dispenser gently mixing all of the powders together.

The compounded pharmaceutical formulation 200 may be stored at controlled room temperature, 15°-30° C. (59°-86° F.) [see USP].

The pharmaceutical formulation 200 should be disposed after 30 days of being compounded.

In one aspect, the pharmaceutical formulation 200 contains dyclonine HCL, triamcinolone, dicyclomine, and dental powder. This pharmaceutical formulation 200 will be in dry form so as to be able to be sprayed through the sprayer 400 of an apparatus.

In one aspect, pharmaceutical formulation 200 contains dyclonine HCL in a dry form in an amount between 75 mg and 125 mg, triamcinolone is an amount between 40 mg and 60 mg, dicyclomine is an amount between 40 mg and 60 mg, and dental powder is an amount between 250 mg and 325 mg, the pharmaceutical formulation 200 being in a dry powder form. The amount of these ingredients in this pharmaceutical formulation 200 should provide treatment of ulcers in the mouth for thirty days.

In one aspect, the dyclonine HCL is an amount of 100 mg, the triamcinolone is an amount of 50 mg, the dicyclomine is an amount of 50 mg, and the dental powder is an amount of 300 mg, the pharmaceutical formulation 200 being in a dry powder form. The amount of these ingredients in this pharmaceutical formulation 200 should provide treatment of ulcers in the mouth for thirty days.

A person with ulcers will be able to apply the pharmaceutical formulation 200 to treat an ulcer in their own mouth or in the mouth of another. A person with mouth ulcers will use an apparatus with a bottle 100 that is filled with the pharmaceutical formulation 200 and will spray the pharmaceutical formulation 200 to the afflicted area. Preferably, the person will spray the afflicted area with one spray four times a day for thirty days.

A person with a mouth ulcer or other mouth sore will be able to apply the pharmaceutical formulation 200 to treat an ulcer in their own mouth or in the mouth of another. A person with mouth ulcers will use an apparatus with a bottle 100 that is filled with the pharmaceutical formulation 200 containing dyclonine HCL, triamcinolone, dicyclomine, and dental powder in a ratio of about 2:1:1:6 and will spray the pharmaceutical formulation 200 to the afflicted area. Preferably, the person will spray the afflicted area with one spray four times a day for thirty days.

Figure 2:
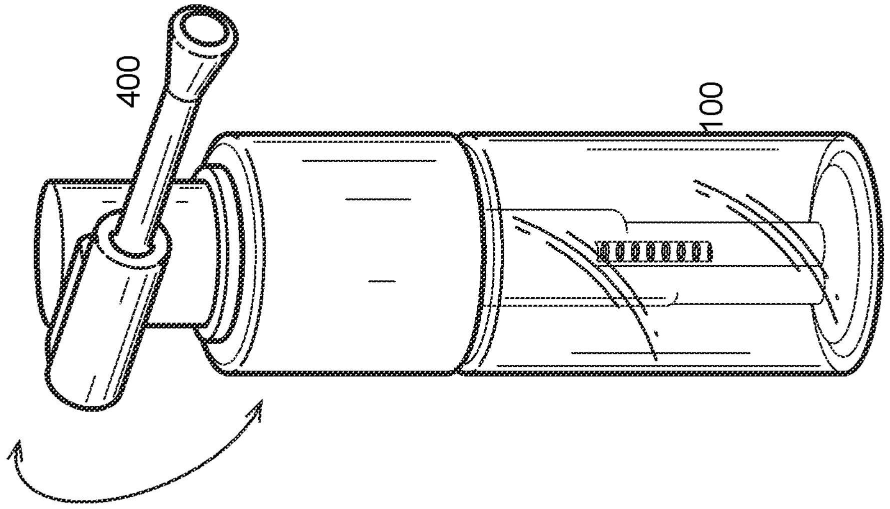
FIG. 2 is an apparatus with an adjustable nozzle in the use position.
Figure 3:
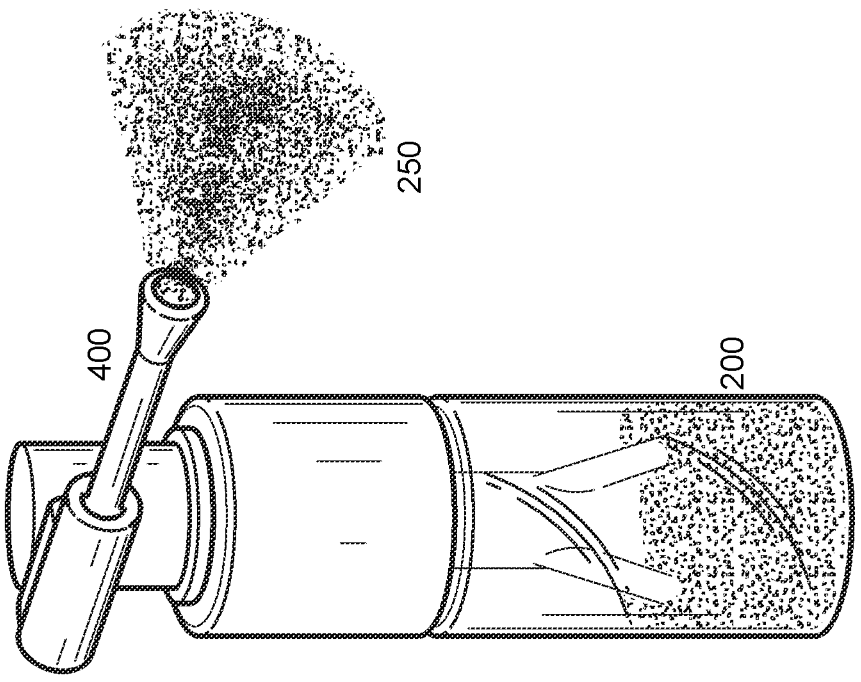
FIG. 3 is an apparatus containing a pharmaceutical formulation.

The present disclosure describes a kit containing an apparatus that contains a pharmaceutical formulation 200. The apparatus has a bottle 100 with an adjustable nozzle 300, and a sprayer 400. FIG. 1 illustrates the apparatus with the adjustable nozzle 300 in a closed position or stored position. This position does not allow the release of the pharmaceutical formulation 200 from the bottle 100. FIG. 2 illustrates the apparatus with the adjustable nozzle 300 in an open position or in the use position. This position allows the sprayer 400 to spray an amount of the pharmaceutical formulation 200 in dry form, which is depicted in FIG. 3.

In one aspect, the pharmaceutical formulation 200 contains an oral anesthetic, a corticosteroid, an anticholinergics/antispasmodics, and dental powder. This pharmaceutical formulation 200 will be in dry form so as to be able to be sprayed through the sprayer 400 of an apparatus. In one aspect, the oral anesthetic is an amount between 75 mg and 125 mg. In one aspect, the oral anesthetic is an amount of 100 mg. In one aspect, the corticosteroid is an amount between 40 mg and 60 mg. In one aspect, the corticosteroid is an amount of 50 mg. In one aspect, the anticholinergics/antispasmodics is an amount between 40 mg and 60 mg. In one aspect, the anticholinergics/antispasmodics is an amount of 50 mg. In one aspect, the dental powder is an amount between 250 mg and 325 mg. In one aspect, the dental powder is an amount of 300 mg.

In one aspect, the pharmaceutical formulation 200 contains an oral anesthetic, a corticosteroid, an anticholinergics/antispasmodics, and dental powder in a ratio of about 2:1:1:6.

A person with ulcers will be able to apply the pharmaceutical formulation 200 containing an oral anesthetic, a corticosteroid, an anticholinergics/antispasmodics, and dental powder to treat an ulcer in their own mouth or in the mouth of another. A person with mouth ulcers will use an apparatus that is filled with the pharmaceutical formulation 200 and will spray the pharmaceutical formulation 200 to the afflicted area. Preferably, the person will spray the afflicted area with one spray four times a day for thirty days.

A person with mouth ulcers will be able to apply the pharmaceutical formulation 200 containing an oral anesthetic, a corticosteroid, an anticholinergics/antispasmodics, and dental powder to treat a mouth ulcer, or other mouth sore, in their own mouth or in the mouth of another. A person with a mouth ulcer will use an apparatus with a bottle 100 that is filled with the pharmaceutical formulation 200 containing oral anesthetic, a corticosteroid, an anticholinergics/antispasmodics, and dental powder in a ratio of about 2:1:1:6 and will spray the pharmaceutical formulation 200 to the afflicted area. Preferably, the person will spray the afflicted area with one spray four times a day for thirty days.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Unless stated otherwise, it should not be assumed that multiple features, embodiments, solutions, or elements address the same or related problems or needs.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

The invention claimed is:

1. A kit comprising:

an apparatus comprising a bottle, an adjustable nozzle, a sprayer, and a dry powder formulation comprising an amount of dyclonine HCL that is between 75 mg to 125 mg, an amount of triamcinolone that is between 40 mg to 60 mg, an amount of dicyclomine that is between 40 mg to 60 mg, and an amount of dental powder that is between 250 mg to 325 mg.

2. The kit of claim 1 wherein the amount of dyclonine HCL is 100 mg.

3. The kit of claim 1 wherein the amount of triamcinolone is 50 mg.

4. The kit of claim 1 wherein the amount of dicyclomine is 50 mg.

5. The kit of claim 1 wherein the amount dental powder is 300 mg.

6. The kit of claim 1 wherein the formulation comprises 100 mg of dyclonine HCL, 50 mg of triamcinolone, 50 mg of dicyclomine, and 300 mg of dental powder.

7. The kit of claim 1, wherein the formulation is dyclonine HCL, triamcinolone, dicyclomine, and dental powder in a ratio of 2:1:1:6.

* * * * *